United States Patent [19]

Yamada et al.

[11] Patent Number: 4,578,172
[45] Date of Patent: Mar. 25, 1986

[54] AIR/FUEL RATIO DETECTOR

[75] Inventors: Tetsusyo Yamada; Shintaro Hirate, both of Aichi, Japan

[73] Assignees: NGK Spark Plug Co.; Mitsubishi Denki K.K., both of Japan

[21] Appl. No.: 681,337

[22] Filed: Dec. 13, 1984

[30] Foreign Application Priority Data

Dec. 15, 1983 [JP] Japan .............................. 58-237626
Aug. 17, 1984 [JP] Japan .............................. 59-172114
Aug. 17, 1984 [JP] Japan .............................. 59-172115

[51] Int. Cl.$^4$ ............................................. G01N 27/58
[52] U.S. Cl. ..................... 204/412; 60/276; 123/489; 204/406; 204/425; 204/426; 338/34
[58] Field of Search ............... 204/412, 410, 424, 425, 204/426, 427, 428, 429, 15, 406; 60/276; 123/489; 338/34

[56] References Cited

U.S. PATENT DOCUMENTS

| | | | |
|---|---|---|---|
| 4,187,486 | 2/1980 | Takahasi et al. | 338/34 |
| 4,224,113 | 9/1980 | Kimura et al. | 204/1 T |
| 4,264,425 | 4/1981 | Kimura et al. | 204/412 |
| 4,298,573 | 11/1981 | Fujishiro | 204/412 X |
| 4,450,065 | 5/1984 | Yamada et al. | 204/412 |

Primary Examiner—G. L. Kaplan

Attorney, Agent, or Firm—Sughrue, Mion, Zinn, Macpeak & Seas

[57] ABSTRACT

An air/fuel ratio detector capable of producing an unambiguous output for both fuel-rich and fuel-lean regions. A solid-electrolyte oxygen-concentration-difference-actuated electrochemical cell sensor element is provided having a porous electrode formed on both sides of an oxygen-ion-conductive solid electrolyte. A solid-electrolyte oxygen pump element is also provided with a porous electrode formed on both sides of an oxygen-ion-conductive solid electrolyte. An oxygen reference element has a metal oxide semiconductor layer formed on one side of a substrate made of an air-impermeable member. The electrochemical cell sensor element and the pump element are disposed facing one another with a small gap therebetween. An air compartment open to the atmosphere is formed between that side of the pump element opposite the side facing the small gap and the side of the reference element opposite the side having the metal oxide semiconductor layer. The air/fuel ratio is detected both by a change in the electrical properties of the oxygen reference element and by output signal provided by at least one of the electromotive force of the electrochemical cell sensor element and a pump current flowing through the pump element.

6 Claims, 20 Drawing Figures

AIR/FUEL RATIO DETECTOR

BACKGROUND OF THE INVENTION

The present invention relates to an A/F (Air/Fuel) ratio detector for use in the measurement or control of the concentration of oxygen in exhaust gas from a burning device such as an internal combustion engine or gas burner.

An oxygen sensor composed of an ion-conductive solid electrolyte (e.g., stabilized zirconia) coated with porous electrode layers (e.g., Pt porous layers) is capable of detecting the concentration of oxygen near a theoretical (stoichiometric) A/F ratio of exhaust gas from an internal combustion engine to thereby detect the combustion efficiency of the engine. Detection is carried out by sensing a change in an electromotive force that is produced by the difference between the partial oxygen pressure of the exhaust gas and that of atmospheric air. This type of oxygen sensor is presently used in numerous applications, for example, in an automobile for the purpose of controlling its internal combustion engine to run at the theoretical air/fuel ratio.

The conventional oxygen sensor exhibits a large amount of change in its output if the operating A/F ratio (which is the weight ratio of air to fuel) is near the theoretical value of 14.7, but otherwise the resulting change in output is negligibly small. Therefore, the output from this sensor cannot be effectively used for an engine operating at an A/F ratio other than near the theoretical value.

Japanese Published Unexamined Patent Application No. 153155/1983 shows an oxygen concentration detector composed of a pair of oxygen-ion-conductive solid electrolyte plates each having an electrode layer on both sides in a selected area close to one end thereof. The two plates are fixed parallel to each other and spaced to provide a gap in an area corresponding to that selected area having the electrode layers. One electrolyte plate with electrode layers is used as an oxygen pump element, and the other plate also having electrode layers is used as an electrochemical cell sensor element that operates in response to the difference in oxygen concentration between the ambient atmosphere and the gap between the two plates. This type of detector has a quick response, but according to experiments conducted by the present inventors, the output of the sensor is ambiguous. That is, when this device is operated in a fuel-rich region having an A/F ratio lower than the theoretical value of 14.7, the direction of change of the output away from the theoretical value is the same as that for operation in the fuel-lean region. Because of the existence of two possible A/F ratios for a single output, the sensor can be used only when it is definitely known whether the burning device to be controlled is operating in the fuel-rich or fuel-lean region. It has been found that it is very difficult to use this detection device for detecting A/F ratio at or near the theoretical ratio, thereby making precise control over the combustion device with a quick response difficult.

SUMMARY OF THE INVENTION

Accordingly, an object of the present invention is to provide an A/F ratio detector that is capable of accurately detecting and with a quick response the operating A/F ratio of a burner such as an internal combustion engine whether it is operating in the fuel-rich region, fuel-lean region or at the theoretical A/F ratio.

Another object of the present invention is to provide an A/F ratio detector that enables precise and simple feedback control over the A/F ratio.

An air/fuel ratio detector according to one embodiment of the present invention comprises a solid electrolyte, an oxygen-concentration-difference-actuated electrochemical cell sensor element which has a porous electrode formed on both sides of an oxygen-ion-conductive solid electrolyte, a solid-electrolyte oxygen pump element which also has a porous electrode formed on both sides of an oxygen-ion-conductive solid electrolyte, and an oxygen reference element having a metal oxide semiconductor layer formed on one side of a substrate made of an air-impermeable material, the electrochemical cell sensor element and the pump element being disposed to face each other with a small gap therebetween, an air compartment which is open to the atmosphere being formed between that side of the pump element opposite the side facing the small gap and that side of the reference element opposite the side having the metal oxide semiconductor layer, the A/F ratio being detected both by a change in electrical properties as provided by the oxygen reference element and by an output signal provided by either the electromotive force of the electrochemical cell element or a pump current flowing through the pump element.

An A/F ratio detector according to another embodiment of the present invention comprises an oxygen pump element which has a porous electrode formed on both surfaces of the sensing end of an oxygen-ion-conductive solid electrolyte and which has on one side thereof an air compartment that is open to the atmosphere and allows the electrode on that side to be exposed to the atmosphere, an oxygen-concentration-difference-actuated electrochemical cell sensor element which also has a porous electrode formed on both surfaces of the sensing end of an oxygen-ion-conductive solid electrolyte and which is disposed a small distance apart from the pump element on the side opposite to that where the air compartment is formed, and a stoichiometric A/F ratio detector element which is positioned side by side with respect to the pump and sensor elements and which has a metal oxide semiconductor layer formed on the surface of an electrically insulating substrate.

An A/F ratio detector according to a further embodiment of the present invention comprises an oxygen pump element which has a porous electrode formed on both surfaces of the sensing end of an oxygen-ion-conductive solid electrolyte and which has on one side thereof an air compartment that is open to the atmosphere and allows the electrode on that side to be exposed to the atmosphere, and an oxygen-concentration-difference-actuated electrochemical cell sensor element which also has a porous electrode formed on both surfaces of the sensing end of an oxygen-ion-conductive solid electrolyte and which is disposed a small distance apart from the pump element on the side opposite to that where the air compartment is formed, the solid electrolyte of the pump element or electrochemical cell sensor element having a metal oxide semiconductor layer formed at the sensing end thereof with an electrically insulating layer or sheet being disposed between either element and the metal oxide semiconductor layer, the A/F ratio being detected both by a change in electrical properties of the metal oxide semiconductor and by an output signal as provided by either a pump current flowing through the pump element or the electromotive force of the electrochemical cell sensor element.

With the arrangements described above, the detector of the present invention has the advantage of requiring only one sensor probe for achieving the detection of an accurate value of the A/F ratio for all or part of the operating range, including both the fuel-rich and fuel-lean regions.

DESCRIPTION OF THE PREFERRED EMBODIMENTS

Embodiment 1

Figure 1:
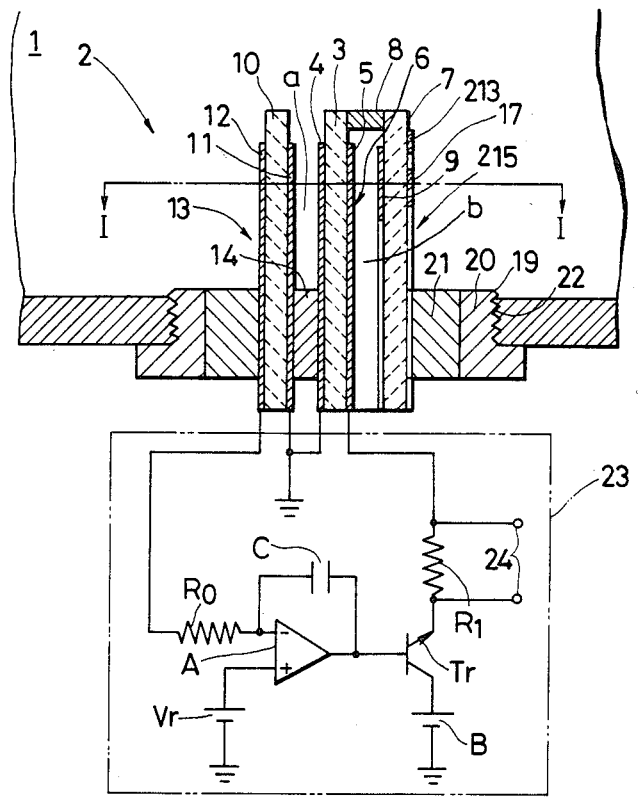
FIG. 1 shows, in cross section, an A/F ratio detector according to a first embodiment of the present invention and, in an electrical schematic diagram, an operating circuit for the A/F ratio detector.
Figure 2:
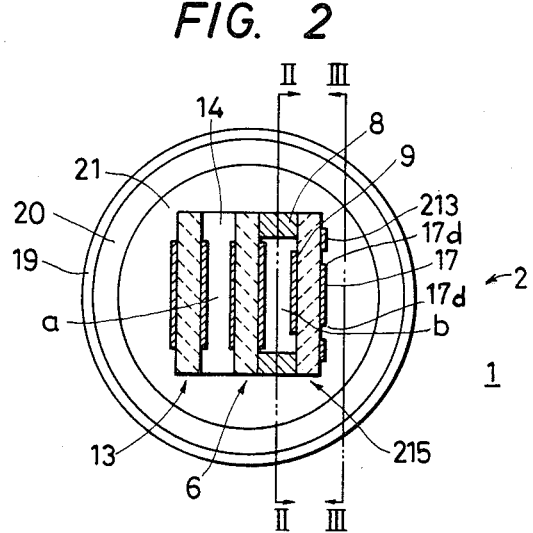
FIG. 2 is a cross section taken along a line I—I in FIG. 1.

The A/F ratio detector according to a first embodiment of the present invention will now be described with reference to FIGS. 1 to 4.

The detector has a probe section 2 which is mounted in an exhaust pipe 1 in an internal combustion engine. The probe 2 is composed of a solid-electrolyte oxygen pump element 6, a solid-electrolyte oxygen-concentration-difference-actuated electrochemical cell sensor element 13 and an oxygen reference element 215. The pump element 6 consists of an ion-conductive solid electrolyte plate 3 (about 0.5 mm thick and preferably made of stabilized zirconia) having porous platinum electrode layers 4 and 5 formed on opposite sides in a thickness of about 20 μm by a thick-film deposition technique. The electrochemical cell sensor element 13 has a similar structure to that of the pump element 6; it consists of an ion-conductive solid-electrolyte plate 10 (about 0.5 mm thick and preferably made of stabilized zirconia) having porous platinum electrode layers 11 and 12 formed on opposite sides in a thickness of about 20 μm by a thick-film deposition technique. The oxygen reference element 215 consists of a substrate plate 7 made of an air-impermeable electrically insulating material such as a ceramic which has a metal oxide semiconductor layer, for instance, a titania element 17, formed on one side in a thickness of about 50 μm by a thick-film deposition technique. The substrate 7 has electric heaters 9 and 213 on opposite sides for holding the titania element 17 at a high temperature. The titania element 17 is disposed in the center of one side of the substrate 7, the electric heater 213 is disposed around the titania element 17 a certain distance apart therefrom to avoid contact with the periphery 17d, and the electric heater 9 is disposed on the other side of the substrate 7 in an area corresponding to the titania element 17. The pump element 6 and the electrochemical cell sensor element 13 are mounted side by side in the exhaust pipe 1 so that they form a small gap a of a size of about 0.1 mm or less. The two elements are fixed together by filling the gap at the base portion with a heat-resistant and electrically insulating spacer 14 (which may be an adhesive filler). That side of the pump element 6 where the porous Pt electrode layer 5 is formed and that side of the oxygen reference element 215 where the electric heater 9 is provided define an air compartment b which is open to the atmosphere. The pump element 6 is sealed to the reference element 215 by a heat-resistive spacer 8 which is disposed on the three sides, (all sides except for the bottom side) of each element. Therefore, the pump element 6 is bonded to the electrochemical cell sensor element 13 and to the reference element 215 by spacers 14 and 8, respectively. A support 20 with a male thread 19 is fixed around the base portion of the so-combined elements 6, 13, and 215 by means of a heat-resistive and electrically insulating adhesive member 21. The probe 2 is securely mounted in the exhaust pipe 1 by engaging the male thread 19 with a female thread 22 in the exhaust pipe 1.

The A/F ratio detector probe 2 having the construction shown above may most advantageously be fabricated by the following procedure: A generally U-shaped green sheet of a material (e.g., ceramic spinel) for forming the spacer 8 is sandwiched between two green sheets, one being made of zirconia solid electrolyte for forming the pump element 6 and which is provided on both sides with a pattern of Pt electrode and associated leads printed by a thick-film deposition technique, and the other being made of, for example, spinel for forming the oxygen reference element 215 and which is provided with a predetermined pattern of Pt resistor material serving as heaters and associated leads, as well as a Pt electrode for a metal oxide semiconductor (e.g., titania), these patterns being printed by a thick-film deposition technique. The three green sheets as placed one on another are pressed together and sintered to form a tubular member. The above-described thick film of metal oxide semiconductor is formed by baking in a sintering atmosphere after sintering of the tubular member. Another green sheet made of zirconia solid electrolyte which has been provided on both sides with a Pt electrode and associated leads by printing is sintered to form an electrochemical cell sensor element 13 in a planar form. The pump element side of the tubular member and the planar electrochemical cell sensor element 13 are placed side by side with a thickness gauge inserted therebetween, and the two elements are fixed together by filling the gap at the base portion with a spacer (or heat-resistive ceramic adhesive agent) 14.

Figure 3:
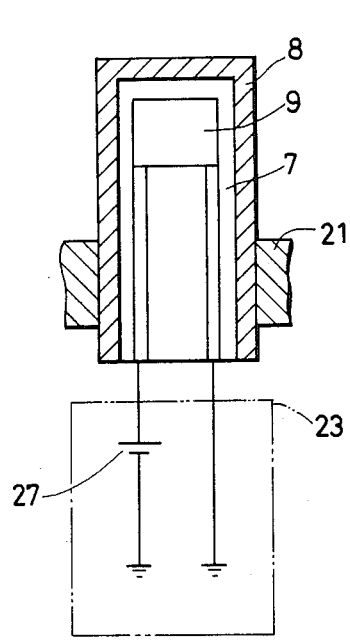
FIG. 3 is a cross section taken along a line II—II in FIG. 2.
Figure 4:
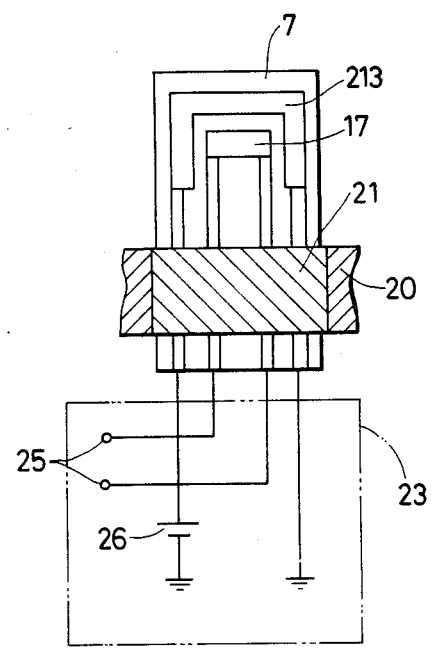
FIG. 4 is a cross section taken along a line III—III in FIG. 2.

An example of an electronic control unit for use in association with the detector according to the first embodiment of the present invention is indicated in FIG. 1 by reference numeral 23. The EMF e generated between the porous Pt electrode layers 11 and 12 of the electrochemical cell sensor element 13 is applied to the inverting input terminal of an operational amplifier A through a resistor $R_0$, and the amplifier produces an output proportional to the difference between e and a reference voltage $V_r$ applied to the noninverting input terminal of the amplifier. The output of the amplifier drives a transistor Tr to control the pump current $I_p$ flowing between the porous Pt electrode layers 4 and 5 of the pump element 6 in such a manner that $I_p$ is sufficient to maintain the EMF e at the constant level $V_r$. The unit 23 also includes a resistor $R_1$ to provide output terminals 24 with an output signal corresponding to the pump current $I_p$ supplied from a d.c. source B. The output of the amplifier A and its inverting input are connected by a capacitor C. The unit 23 also has output terminals 25 (FIG. 4) upon which is generated a signal indicative of changes in the electrical resistance of the titania element 17 occurring in response to changes in the differential oxygen concentration in the exhaust pipe 1 as detected by the oxygen reference element 215. Electric heaters 213 and 9 for heating the titania element 17 in the exhaust pipe 1 are connected to respective power sources 26 (FIG. 4) and 27 (FIG. 3).

Embodiment 2

Figure 8:
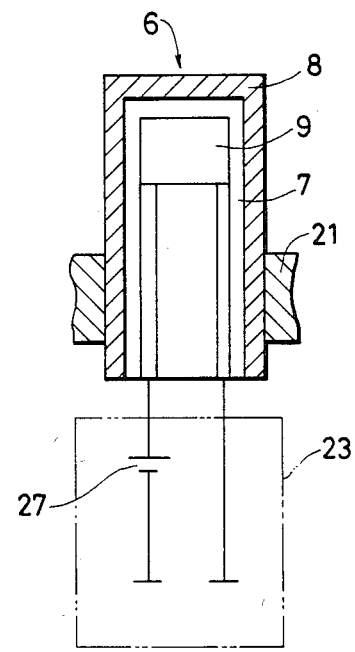
FIG. 8 is a cross section taken along a line III—III in FIG. 6.

The A/F ratio detector according to a second embodiment of the present invention is shown in FIGS. 5 to 8. The detector has a probe section 2 which is mounted in an exhaust pipe 1 of an internal combustion engine. The probe 2 has a solid-electrolyte oxygen pump element 6 which consists of an ion-conductive solid-electrolyte plate 3 (about 0.5 mm thick and preferably made of stabilized zirconia) having porous platinum electrode layers 4 and 5 formed on opposite sides of the sensing end in a thickness of about 20 $\mu$m by a thick-film deposition technique. The pump element 6 has an air compartment b on one side (on the side of Pt electrode layer 5 in the embodiment shown), which is open only at the bottom so that the Pt electrode layer 5 is exposed to the atmosphere. The other members that define the compartment are ceramic wall members 7 and 8 which are typically made of stabilized zirconia, alumina or spinel. The member 7 faces the solid electrolyte plate 3 and forms one of the two major walls of the air compartment, whereas the member 8 connects the solid electrolyte plate 3 and the wall member 7 on three sides as shown in FIG. 8. The side of wall member 7 which faces the air compartment is provided with an electric heater 9 for heating the sensing end of the solid electrolyte plate 3 in the pump element 6. The A/F ratio detector probe 2 also has a solid-electrolyte oxygen-concentration-difference-actuated electrochemical cell element 13 which, as in the case of the pump element 6, consists of an ion-conductive solid-electrolyte plate 10 (about 0.5 mm thick and preferably made of stabilized zirconia) having porous platinum electrode layers 11 and 12 formed on opposite sides of the sensing end in a thickness of about 20 $\mu$m by a thick-film deposition technique.

The pump element 6 and the electrochemical cell sensor element 13 are mounted side by side in the exhaust pipe 1 with a small gap a of a size of about 0.1 mm or less, and the two elements are fixed together by filling the gap at the base portion with a heat-resistant and electrically insulating spacer 14 (which may be an adhesive filler).

Figure 5:
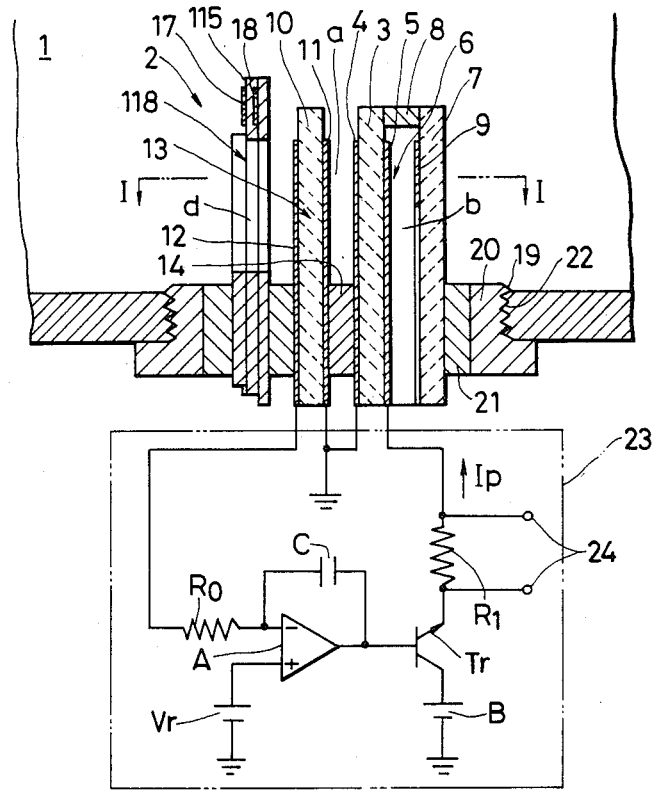
FIG. 5 shows, in cross section, an A/F ratio detector according to a second embodiment of the present invention.
Figure 6:
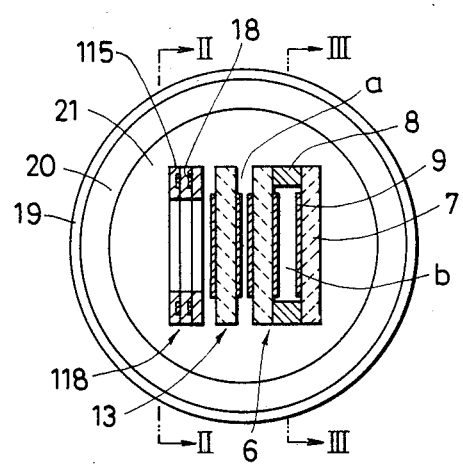
FIG. 6 is a cross section taken along a line I—I in FIG. 5.
Figure 7:
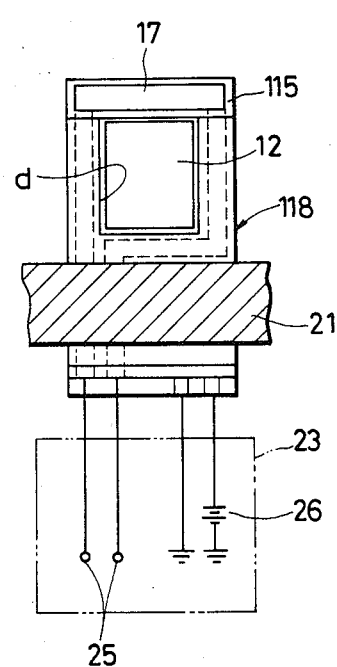
FIG. 7 is a cross section taken along a line II—II in FIG. 6.

The probe 2 of the detector shown in FIG. 5 has a third component, namely, a stoichiometric A/F ratio detecting element 118. The element 118 includes a substrate plate 115 made of electrically insulating material such as ceramic and which has a metal oxide semiconductor (i.e., titania) element 17 formed on one side of the sensing end of the substrate in a thickness of about 50 $\mu$m by a thick-film deposition technique. The substrate 115 also has in its interior an electric heater 18 that is placed closely adjacent to the titania element 17 for maintaining it at elevated temperatures. The heater and titania element are integrally bonded to the substrate to form a single assembly, i.e., the stoichiometric A/F ratio detecting element 118. The oxygen pump element 6 connected to the electrochemical cell sensor element 13 to form the small gap a is positioned closely adjacent to or a suitable distance away from the detecting element 118, and the three elements are attached to a support 20 at their outer base portions by means of a heat-resistive and electrically insulating member 21. The support 20 is provided with a male thread 19. The substrate 115 forming the detecting element 118 is provided with a window d in an area close to the sensing end. This window permits the gas under analysis to contact easily the electrode layer 12 on the electrochemical cell sensor element 13. The probe 2 is securely mounted in the exhaust pipe 1 by engaging the male thread 19 with a female thread 22 in the exhaust pipe 1.

The assembly of the pump element 6 and the electrochemical cell element 13 as one component of the detector probe 2 may advantageously be fabricated by the following procedure: A U-shaped green sheet of ceramic spinel which is to form the side wall 8 for the air compartment is sandwiched between one green sheet of zirconia solid electrolyte for forming the pump element 6 and another green sheet which is typically made of ceramic spinel and which is to form the main wall for the air compartment. The first green sheet is provided on both sides with a predetermined pattern of a platinum electrode layer and associated leads that is printed by a thick-film deposition technique, whereas the second green sheet is provided on one side with platinum resistor material in a predetermined pattern (forming heater 9) and associated leads, also printed by a thick-film deposition technique. The U-shaped green sheet is bonded to green sheets by thermal compression and fired to provide a single tubular unit. A green sheet of zirconia solid electrolyte that is provided on both sides in a predetermined pattern with a platinum electrode layer and associated leads formed by a thick-film deposition technique is fired to produce a planar electrochemical cell sensor element 13. The previously fabricated tubular unit and the cell sensor element 13 are placed side by side with a thickness gauge inserted therebetween, and the two elements are then fixed together by filling the gap at the base portion with a spacer (or heat-resistive ceramic adhesive agent) 14.

The stoichiometric A/F ratio detecting element 118 may advantageously be prepared by the following procedure: A first green sheet, typically made of alumina, is provided with a predetermined pattern of a platinum resistor material (forming heater 18) and associated leads formed by a thick-film deposition technique. Then, a second green sheet is superimposed on the first green sheet with the connecting ends of the leads still exposed. The surface of the second green sheet is provided with a predetermined pattern of platinum electrodes (for connection to metal oxide, e.g., titania) and associated leads formed by a thick-film deposition technique. Then, a third green sheet is superimposed on the second green sheet with the platinum electrode and the connecting ends of the leads remaining exposed. The three green sheets are bonded together by thermal compression and fired to provide the ceramic substrate 115. It is advantageous to form and bake a thick film of metal oxide between the exposed electrodes on the substrate in the sintering atmosphere after sintering of the substrate.

An example of the electronic control unit for use in association with the detector according to the second embodiment of the present invention is indicated in FIG. 5 by reference numeral 23. The EMF e generated between the porous Pt electrode layers 11 and 12 of the electrochemical cell sensor element 13 is applied to the inverting input terminal of an operational amplifier A through a resistor $R_0$, and the amplifier produces an output proportional to the difference between e and a reference voltage $V_r$ applied to the non-inverting input terminal of the amplifier. The output of the amplifier drives a transistor Tr to control the pump current $I_p$ flowing between the Pt electrode layers 4 and 5 on the pump element in such a manner that $I_p$ is sufficient to maintain the EMF e at the constant level $V_r$. The control unit 23 also includes a resistor $R_1$ to provide output terminals 24 with an output signal corresponding to the pump current $I_p$ being supplied from a d.c. source B. The output of the amplifier A and its inverting input are connected by a capacitor C. The unit 23 also has output terminals 25 (FIG. 7) upon which is generated a signal indicative of changes in the electrical resistance of the titania element 17 produced in response to changes in the differential oxygen concentration in the exhaust pipe 1 as detected by the stoichiometric A/F ratio sensing sensor element 118. An electric heater 18 for heating the titania element 17 in the exhaust pipe 1 is connected to a power source 26 (FIG. 7), whereas the heater 9 of the oxygen pump element 6 is connected to a power source 27 (FIG. 8).

Embodiment 3

Figure 12:
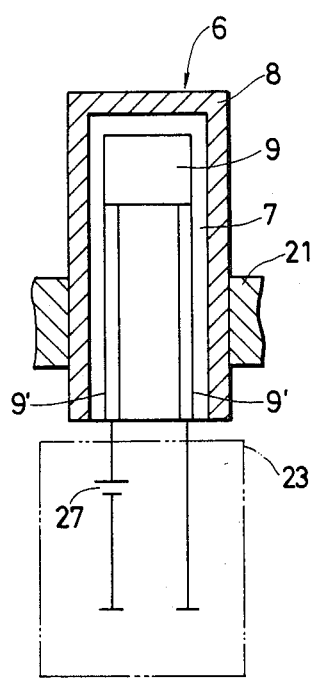
FIG. 12 is a cross section taken along a line III—III in FIG. 10.
Figure 11:
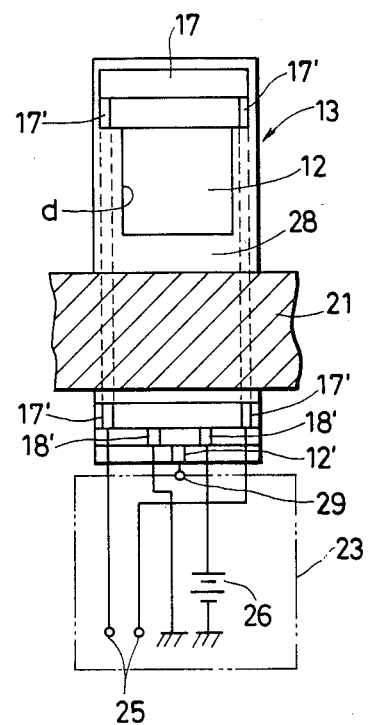
FIG. 11 is a cross section taken along a line II—II in FIG. 10.

The A/F ratio detector according to a third embodiment of the present invention is shown in FIGS. 9 to 12. The detector has a probe section 2 which is mounted in an exhaust pipe 1 of an internal combustion engine. The probe 2 has a solid-electrolyte oxygen pump element 6 which consists of an ion-conductive plate 3 (about 0.5 mm thick and preferably made of stabilized zirconia) having porous platinum electrode layers 4 and 5 formed on opposite sides of the sensing end in a thickness of about 20 μm by a thick-film deposition technique. The pump element 6 has an air compartment b on one side (on the side of the Pt electrode layer 5 in the embodiment shown) which is open only at the bottom so that the Pt electrode layer 5 is exposed to the atmosphere. The other members that define the air compartment are ceramic wall members 7 and 8, which are typically made of stabilized zirconia, alumina or spinel. The member 7 faces the solid electrolyte plate 3 and forms one of the two major walls of the air compartment, whereas the member 8 connects the solid electrolyte plate 3 and the wall member 7 on three sides as shown in FIG. 12. The side of the wall member 7 which faces the air compartment is provided with an electric heater 9 for heating the sensing end of the solid electrolyte plate 3 in the pump element 5.

The A/F ratio detector probe 2 also has a solid-electrolyte oxygen-concentration-difference-actuated electrochemical cell sensor element 13 which, as in the case of the pump element 6, consists of an ion-conductive solid-electrolyte plate 10 (about 0.5 mm thick and preferably made of stabilized zirconia) having porous platinum electrode layers 11 and 12 formed on opposite sides of the sensing end in a thickness of about 20 μm by a thick-film deposition technique. The electrochemical cell sensor element 13 also has the following components: a high heat-conductive, electrically insulating substrate 15 which is disposed on one side of the solid-electrolyte plate 10, for instance, on the side where the porous Pt layer 12 is disposed, and which has a window c conforming with the contour of the Pt layer 12 so that the latter is exposed through the window c, the substrate 15 being in planar form and having a thickness of about 0.25 mm and being made of a highly heat-conductive and electrically insulating material such as alumina or spinel; an electric heater 18 formed around the window c on the side of the highly heat-conductive and electrically insulating substrate 15 opposite to the side in contact with the solid electrolyte plate 10, the heater 18 being spaced both from the periphery of the window c and from the outer edges of the substrate 15; a planar highly heat-conductive and electrically insulating substrate 16 which isolates the heater 18 from the outside, receiving it internally on that side of the substrate 15 where the heater 18 is disposed, the substrate 16 having a window d which, like the window c, conforms with the contour of the Pt layer 12 so that the latter is exposed through the window d; a titania element 17 which is a metal oxide semiconductor layer formed in a thickness of about 50 μm by a thick-film deposition technique above the window d on that side of the substrate 16 opposite to the side where the heater 18 is received internally; leads 4', 5', 9', 11', 12', 17' and 18' by which respective components of the pump element 6 and electrochemical cell sensor element (4, 5, 9, 11, 12, 17 and 18) are connected electrically to an external control circuit (to be described later) and which are formed by a thick-film deposition technique; and a planar, highly heat-conductive and electrically insulating substrate 28 which insulates and protects the leads 17' formed on the substrate 16 for providing electrical connection between the semiconductor layer 17 and the external control unit.

The pump element 6 and the electrochemical cell sensor element 13 are mounted side by side in the exhaust pipe 1 with the Pt electrode layer 4 and the Pt layer 11 forming a gap a of 0.1 mm or less therebetween, and the two elements are fixed together by filling the gap at the base portion with a heat-resistance and insulating spacer 14. An adhesive filler may be used as the spacer. A support 20 with a male thread 19 is fixed around the base portion of the so-combined pump element 6 and sensor element 13 by means of a heat-resistive and insulating adhesive member 21. The probe 2 is securely mounted in the exhaust pipe 1 by engaging the male thread 19 with a female thread 22 in the exhaust pipe 1.

The detector probe 2 having the construction shown above may most advantageously be fabricated by the following procedure: A U-shaped green sheet of ceramic spinel which is to form the side wall 8 for the air compartment is sandwiched between one green sheet of zirconia solid electrolyte for forming the pump element 6 and another green sheet which is typically made of spinel and which is to form the main wall 7 for the air compartment. The first green sheet is provided on both sides with a platinum electrode layer in a predetermined pattern and associated leads printed by a thick-film deposition technique, whereas the other green sheet is provided on one side with platinum resistor material (forming heater 9) in a predetermined pattern and associated leads also printed by a thick-film deposition technique. The U-shaped green sheet is bonded to the green sheets by thermal compression and fired to provide a single tubular unit. Subsequently, a green sheet of zirconia solid electrolyte that is provided on both sides with a platinum electrode layer in a predetermined pattern and associated leads printed by thick-film deposition technique is prepared. An electric heater made of a platinum resistor material and associated leads which are sandwiched between two tightly heat-conductive and electrically insulating substrates, for example, two tabular green spinel sheets each having a window, are pressed onto one side of the prepared green zirconia sheet. Then, a predetermined pattern of lead wires for a metal oxide semiconductor layer is formed by a thick-film deposition technique on the surface of the heat-conductive and insulating substrate that is opposite the substrate which is in direct contact with the zirconia electrolyte sheet. Subsequently, a green spinel sheet is placed over the substrate to insulate the lead wires, and the entire assembly is then thermally compressed and sintered to provide an oxygen-concentration-difference-actuated electrochemical cell sensor element 13. It is preferable to form and bake a thick film of the metal oxide between the leads in a sintering atmosphere after the sintering of the element. The pump element 6 and cell sensor element 13 are mounted side by side with a thickness gauge inserted therebetween, and the two elements 6 and 13 are fixed together by filling the gap at the base portion with a spacer (or heat-resistive ceramic adhesive agent) 14.

Figure 9:
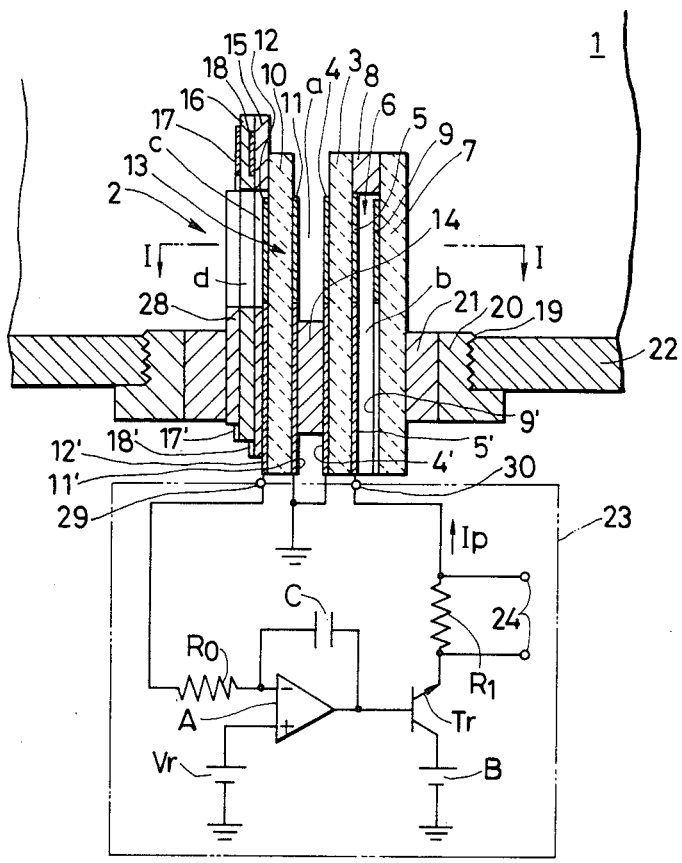
FIG. 9 shows, in cross section, an A/F ratio detector according to a third embodiment of the present invention and, in an electrical schematic diagram, an operating circuit for the A/F ratio detector.
Figure 10:
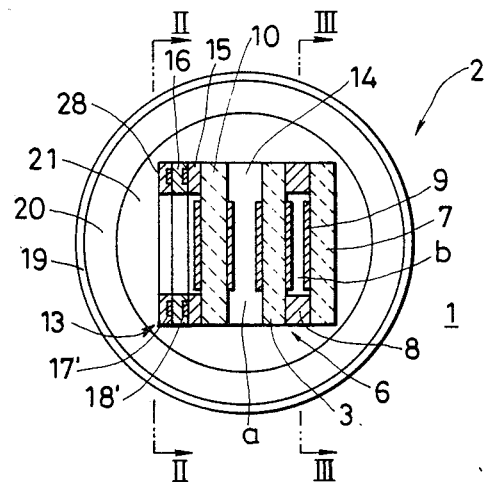
FIG. 10 is a cross section taken along a line II—II in FIG. 9.

An example of the electronic control unit for use in association with the detector of the third embodiment is indicated in FIG. 9 by reference numeral 23. The EMF e generated between the porous Pt electrode layers 11 and 12 on the electrochemical cell element 13 is applied to the inverting input terminal of an operational amplifier A through a resistor $R_0$. The amplifier A produces an output proportional to the difference between e and a reference voltage $V_r$ applied to the noninverting input terminal of the amplifier. The output of the amplifier drives a transistor Tr to control the pump current $I_p$ flowing between the Pt electrode layers 4 and 5 of the pump element 6 in such a manner that $I_p$ is sufficient to maintain the EMF e at the constant level $V_r$. The control unit 23 also includes a resistor $R_1$ to provide output terminals 24 with an output signal proportional to the pump current $I_p$ supplied from a d.c. source B. The output of the amplifier A and its inverting input are connected by a capacitor C. The control unit 23 also has output terminals 25 upon which are generated a signal indicative of changes in the electrical resistance of the titania element 17 occurring in response to changes in the differential oxygen concentration in the exhaust pipe 1. An electric heater 18 for heating the titania element 17 in the exhaust pipe 1 is connected to a power source 26 via leads 18'. The heater 9 of the oxygen pump element 6 is connected to a power source 27 via leads 9'.

Figure 13:
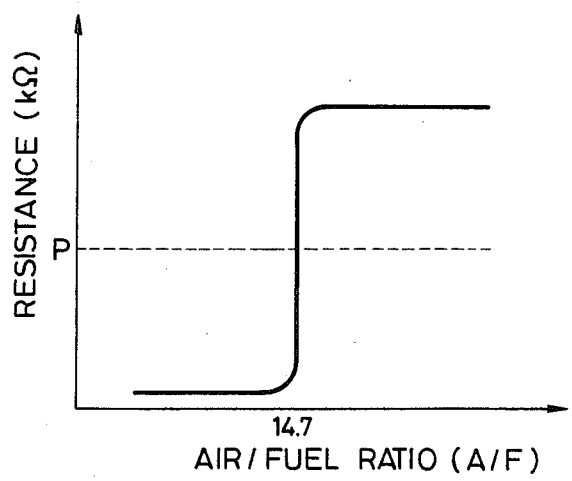
FIG. 13 is a characteristic curve showing the profile of A/F ratio vs. the electrical resistance of a metal oxide semiconductor.
Figure 14:
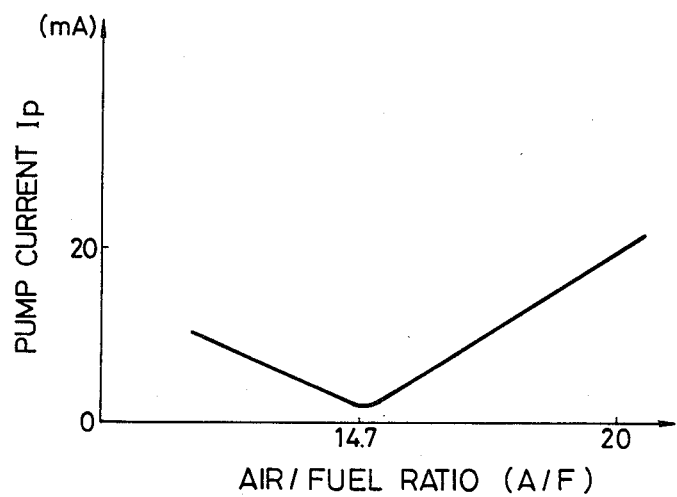
FIG. 14 is a characteristic curve showing the profile of A/F ratio vs. pump-out current $I_p$ flowing through an oxygen pump element, with the EMF (electromotive force) e of an oxygen-concentration-difference-actuated electrochemical cell sensor element held constant.

Two characteristic curves for the A/F ratio detectors shown in FIGS. 1 to 12 are illustrated in FIGS. 13 and 14. FIGS. 13 shows the profile of A/F ratio vs. the electrical resistance of the titania element 17 as measured at the output terminal 25. The resistance is low in the fuel-rich region where the A/F ratio is smaller than the stoichiometric value of 14.7. At about 14.7, there occurs a sudden increase in the resistance, and in the fuel-lean region (A/F>14.7), the resistance assumes a high value. FIG. 14 shows the profile of A/F ratio vs. pump-out current $I_p$ for a reference voltage $V_r$ of, for instance, 20 mV. When the EMF e is at 20 mV, $I_p$ flowing in the pump-out direction decreases with increasing A/F ratio in the fuel-rich region (A/F<14.7), and $I_p$ increases in proportion to the A/F ratio in the fuel-lean region (A/F>14.7).

The detectors according to the embodiments shown in FIGS. 1 to 12 make use of the characteristics depicted in FIGS. 13 and 14. The detector senses both the fuel-rich region (R<P) and the fuel-lean region (R>P), P being a reference point set between maximum and minimum resistance values, and provides an appropriate signal on the output terminals 25 accordingly. When the engine is running in the fuel-rich region, the resistance of the titania element 17 must be smaller than point P, and this information and an output signal corresponding to the resultant pump current $I_p$ flowing through the pump element 6 may be detected so as to achieve fine measurement or control of the A/F ratio for the fuel-rich region. If the engine is operating in the fuel-lean region, the resistance of the titania element 17 must be greater than point P, and this information and an output signal corresponding to the resultant pump current $I_p$ may be detected to perform fine measurement or control of the A/F ratio for the fuel-lean region. If the engine is to be operated at the stoichiometric A/F ratio of 14.7, the resistance of the titania element 17, which drops suddenly as the decreasing A/F ratio approaches 14.7 and which can be detected at output terminal 25, may be used as a direct feedback control signal.

Having the construction shown above, the detector of the present invention enables accurate measurement of the A/F ratio of an engine over a wide range including both the fuel-rich and fuel-lean regions. One application of the detector is in a feedback loop used to maintain a desired value of the A/F ratio.

The proportional change of $I_p$ with A/F ratio in the fuel-lean region is already known and shown in, for example, Japanese Published Unexamined Patent Application No. 153155/1983. The partial pressure of oxygen in the exhaust gas introduced into the gap a is modified by the action of the pump element 6 to a value which differs from the partial pressure of the oxygen in the exhaust gas flowing through the pipe 1. The pump-out current $I_p$ supplied to the pump element 6 is controlled so that the EMF e of the sensor element 13 produced in response to the differential partial oxygen pressure is maintained constant. As a consequence of this control, the pump current $I_p$ changes in proportion to the concentration of oxygen in the exhaust gas. Sensitivity to CO gas is the primary reason for this oxygen pump-out mechanism which occurs in the fuel-lean region.

Figure 15:
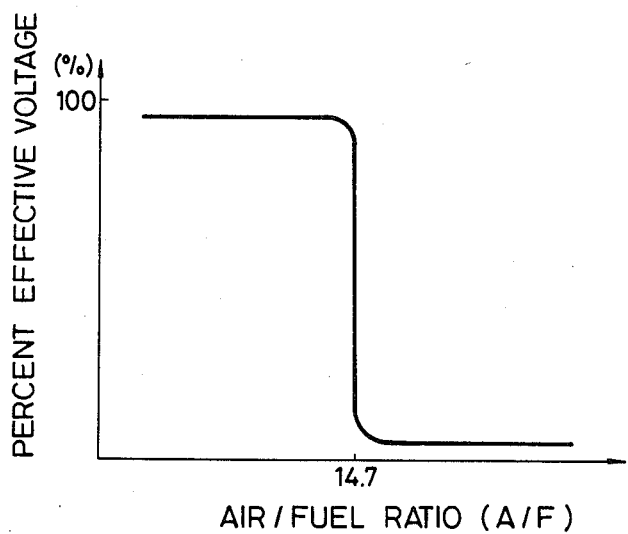
FIG. 15 is a characteristic curve showing the profile of A/F ratio vs. percent effective voltage.

In the three embodiments shown above, the electrical resistance of the titania element 17 is used as a criterion for determining whether the engine is operating in the fuel-rich or fuel-lean region. Alternatively, the change in percent effective voltage, or the proportion of applied voltage that has passed through the titania element 17 combined with a series resistor may be used as the criterion. The profile of A/F ratio vs. the percent effective voltage is depicted in FIG. 15.

Figure 16:
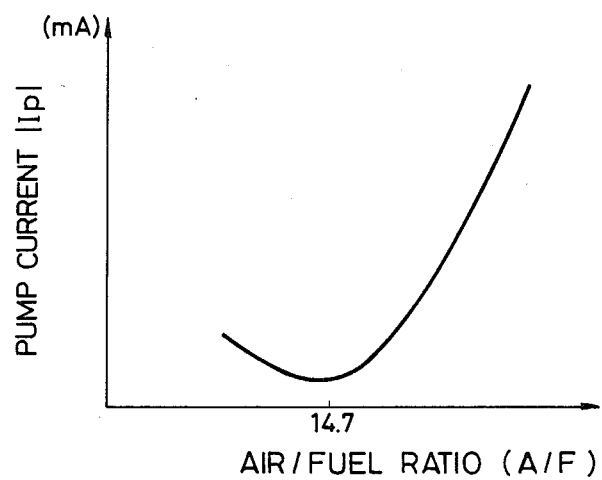
FIG. 16 is a characteristic curve showing the profile of A/F ratio vs. pump-in current $I_p$ flowing through the pump element, with the EMF e of the electrochemical cell sensor element held constant.

In the foregoing embodiments, the pump current $I_p$ flowing through the pump element 6 has a polarity such that oxygen is pumped out of the small gap a ($I_p > 0$). If desired, $I_p$ may be caused to flow in the opposite direction ($I_p < 0$) so that oxygen is pumped into the gap a from the air compartment b. FIG. 16 shows the profile of A/F ratio vs. $I_p$ in this modified case with the output of the electrochemical cell sensor element 13 being held constant. The characteristics shown in FIG. 16 may also be used for the purposes of the present invention since they reflect a certain correlation between the operating A/F ratio and the pump current $I_p$.

When the pump current $I_p$ flowing through the pump element 6 (whether oxygen is pumped into or out of the small gap a) is held constant, the EMF e generated by the sensor element 13 also varies with the A/F ratio, and this correlation may be used for achieving the purposes of the present invention.

Figure 17:
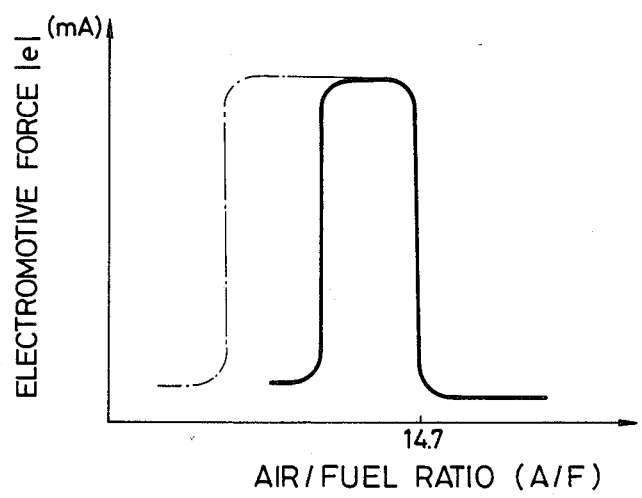
FIG. 17 is a characteristic curve showing the profile of A/F ratio vs. the EMF of the electrochemical cell sensor element with the pump-in current $I_p$ as a parameter.

FIG. 17 shows how the EMF ($e < 0$) of the cell element 13 varies with the A/F ratio when the oxygen pump-in current $I_p$ is taken as a parameter. As shown, the EMF changes abruptly in the fuel-rich region, and the A/F ratio that causes such abrupt change is dependent on the specific $I_p$ setting. This characteristic may be used in order to perform precise feedback control over the A/F ratio in the fuel-rich region. Since the air compartment b provides an ample supply of oxygen into the gap a, the dynamic range of measurement can be expanded to an extremely fuel-rich region.

Embodiment 4

Figure 18:
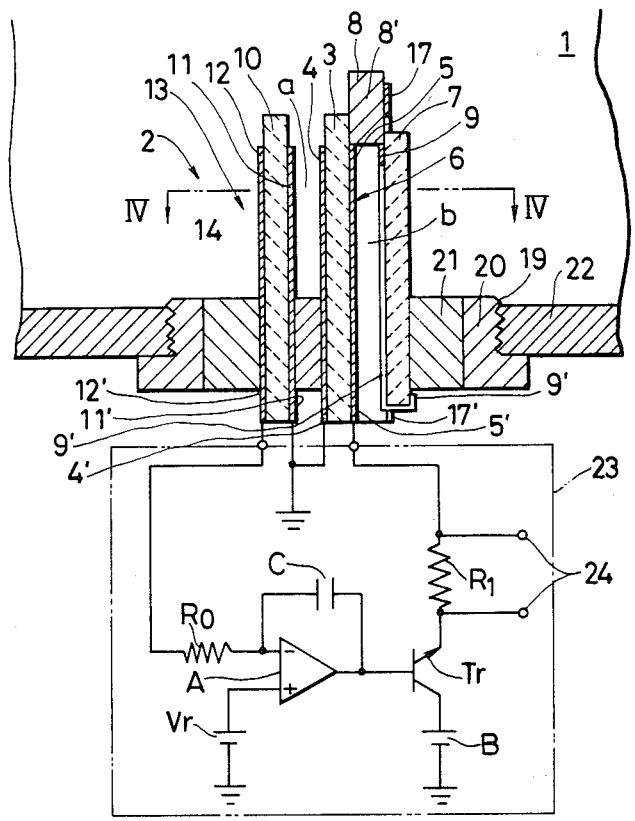
FIG. 18 shows, in cross section, an A/F ratio detector according to a fourth embodiment of the present invention and, in an electrical schematic diagram, an operating circuit for the A/F ratio detector.
Figure 19:
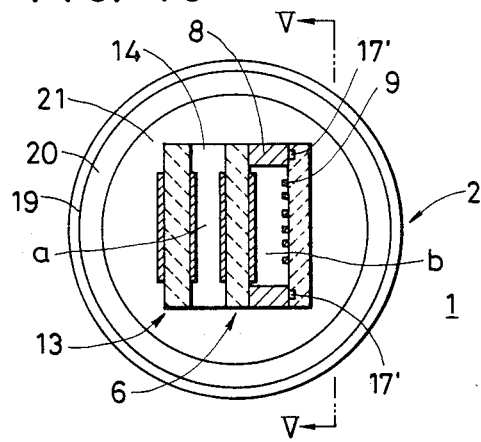
FIG. 19 is a cross section taken along a line IV—IV in FIG. 18.
Figure 20:
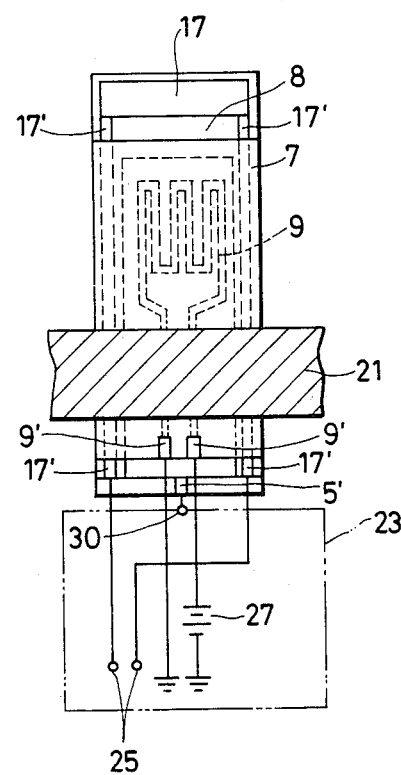
FIG. 20 is a cross section taken along a line V—V in FIG. 19.

FIGS. 18 to 20 illustrate the A/F ratio detector according to a fourth embodiment of the present invention. The fourth embodiment is similar to the third embodiment (FIGS. 9 to 12), so that like parts are identified by like reference numerals or characters and will need no detailed explanation. In this third embodiment, the titania element 17 as a metal oxide semiconductor layer is disposed on the sensing end of the electrochemical cell sensor element 13 which is farther away from the exhaust pipe 1. In the fourth embodiment, the wall member 8 defining the air compartment b in combination with the pump element 6 is positioned to project from the sensing end of the solid electrolyte plate 3, and the projecting part 8' is coated with a metal oxide semiconductor layer 17 for sensing whether the operating A/F ratio is greater or smaller than the stoichiometric value. In the embodiment shown in FIG. 18, the metal oxide semiconductor layer is disposed on that side of the projection 8' which faces the wall member 7 with a view to insulating and protecting the principal part of associated lead wires 17' by that wall member 7. As in the case of the third embodiment, the oxygen pump element 6 in the fourth embodiment can be advantageously fabricated by thermal compression of three green sheets followed by sintering of the assembly.

The third embodiment of the present invention may be modified in several other ways. For example, the highly heat-conductive, electrically insulating substrates 16 and 28 in sheet form as components of the oxygen concentration electrochemical cell sensor element 13 may be replaced by layers prepared by sintering an applied paste of raw ceramic. Alternatively, the sensing end of the solid electrolyte plate 10 of the sensor element 13 may be positioned so that it projects beyond the sensing end of the solid electrolyte plate 3 of the pump element 6, and the surface of the projected area is coated with a highly heat-conductive and thermally insulating substrate 15 which, instead of being in a sheet form, is a layer that is prepared by sintering an applied paste of raw ceramic.

The unique features of the A/F ratio detector according to the embodiments of the present invention are as follows: (1) it ensures an accurate and simple measurement of the A/F ratio over a wide range including values less than 11 and more than 25; (2) it also ensures precise and easy feedback control over the operating A/F ratio of an internal combustion engine; (3) it permits the use of a smaller and more compact sensor probe to be installed on the exhaust pipe; (4) after turning on the power, each functional member of the detector is warmed up so quickly that it can be activated within a very short period of time.

The characteristics shown above that are provided by the detector probe 2 of the present invention may be used either individually or in combination for the purpose of effecting continuous feedback control over the operating A/F ratio throughout the operating range by frequent mode changes.

In the detection probe of the embodiment of the present invention, the pump element and the sensor element are mounted side by side in the exhaust pipe with a gap therebetween and are fixed together by filling the gap at the base portions with a spacer. It is preferable to sufficiently open peripheral edges of the pump element and the sensor element to the exhaust gases so as to increase the responsivity of the probe. However, the present invention is not limited to the configuration of open edges of the pump element and the sensor element except for their base portions. For example, it is possible to provide support members between the solid-electrolyte plates of the pump element and the sensor element for more readily regulating the gap dimensions as far as the support member does not cause any considerable reduction of responsivity.

The gap between the pump element and the sensor element is preferably in a range from 0.01 to 0.15 mm. If the gap is too narrow, the responsivity is reduced. The electrode layer which defines the small gap is preferably a porous thick layer having a mean porosity of about 10–40% (as determined by a porosimeter of the pressurized mercury type) in consideration of its diffusion resistance against component gases such as oxygen.

Furthermore, in the case that the electrode layer is formed by a suitable thin-film deposition technique, it is preferable to provide thereon a porous layer such as a ceramic material to which may be added a catalytic agent for obtaining a catalytic action.

We claim:

1. An air/fuel ratio detector comprising: a solid-electrolyte oxygen-concentration-difference-actuated electrochemical cell sensor element which has a porous electrode formed on both sides of an oxygen-ion-conductive solid electrolyte, a solid-electrolyte oxygen pump element which also has a porous electrode formed on both sides of an oxygen-ion-conductive solid electrolyte, and an oxygen reference element having a metal oxide semconductor layer formed on one side of a substrate which is made of an air-impermeable member, said electrochemical cell sensor element and said pump element being disposed to face each other with a small gap therebetween, an air compartment which is open to the atmosphere being formed between that side of said pump element which is opposite the side facing said small gap and that of said reference element which is opposite the side having said metal oxide semiconductor layer, the air/fuel ratio being detected both by a change in electrical properties as provided by said oxygen reference element and by an output signal as provided by at least one of the electromotive force of said electrochemical cell sensor element and a pump current flowing through said pump element.

2. The air/fuel ratio detector according to claim 1, wherein said oxygen reference element is provided with an electric heater for maintaining said metal oxide semiconductor layer at a high temperature.

3. An air/fuel ratio detector comprising: an oxygen pump element which has a porous electrode formed on both surfaces of a sensing end of an oxygen-ion-conductive solid electrolyte and which has on one side thereof an air compartment that is open to the atmosphere and allows the electrode on that side to be exposed to the atmosphere, an oxygen-concentration-difference-actuated electrochemical cell sensor element which also has a porous electrode formed on both surfaces of a sensing end of an oxygen-ion-conductive solid electrolyte and which is disposed a small distance apart from said pump element on the side opposite to that where said air compartment is formed, and a stoichiometric air/fuel ratio detector element which is positioned side by side with respect to said pump and cell sensor elements and which has a metal oxide semiconductor layer formed on the surface of an electrically insulating substrate.

4. The air/fuel ratio detector according to claim 3, wherein said stoichiometric air/fuel ratio detector element is provided with an electric heater for maintaining said metal oxide semiconductor layer at a high temperature.

5. An air/fuel ratio detector comprising: an oxygen pump element which has a porous electrode formed on both surfaces of a sensing end of an oxygen-ion-conductive solid electrolyte and which has on one side thereof an air compartment that is open to the atmosphere and allows the electrode on that side to be exposed to the atmosphere, and an oxygen-concentration-difference-actuated electrochemical cell sensor element which also has a porous electrode formed on both surfaces of the sensing end of an oxygen-ion-conductive solid electrolyte and which is disposed a small distance apart from said pump element on the side opposite to that where said air compartment is formed, the solid electrolyte of said pump element or electrochemical cell sensor element having a metal oxide semiconductor layer formed at a sensing end thereof with an electrically insulating layer disposed between either element and said metal oxide semiconductor layer, the air/fuel ratio being detected both by a change in electrical properties as provided by said metal oxide semiconductor and by an output signal as provided by at least one of a pump current flowing through said pump element and the electromotive force of said electrochemical cell sensor element.

6. The air/fuel ratio detector according to claim 5, wherein an electric heater for maintaining said metal oxide semiconductor layer at a high temperature is provided on the surface or in the interior of that part of said electrically insulating layer which is closest to said metal oxide semiconductor layer.

* * * * *